(12) United States Patent
Goodman

(10) Patent No.: US 6,355,691 B1
(45) Date of Patent: Mar. 12, 2002

(54) URUSHIOL THERAPY OF TRANSITIONAL CELL CARCINOMA OF THE BLADDER

(76) Inventor: Tobias M. Goodman, 41 East Ave., Westerly, RI (US) 02891

(*) Notice: Subject to any disclaimer, the term of this patent is extended or adjusted under 35 U.S.C. 154(b) by 0 days.

(21) Appl. No.: 09/399,847

(22) Filed: Sep. 21, 1999

Related U.S. Application Data

(60) Provisional application No. 60/108,115, filed on Nov. 12, 1998.

(51) Int. Cl.[7] ........................ A61K 31/05; A61K 31/045
(52) U.S. Cl. ........................................ 514/731; 514/738
(58) Field of Search ................................. 514/731, 738

(56) References Cited

PUBLICATIONS

Osol, Editor–in–Chief of Remington's Pharmaceutical Sciences, p. 772, Jun. 14, 1976.*

Byers, V. S. et al., "Modulation of Tumor Cell Membranes with Lipophilic Haptens: an Approach to Modifying Tumor Immunogenicity", Abstract to ICN–UCLA symp. Mol. Cell. Biol. (1979), 16 (T B Lymphocytes: Recognition Funct.), 603–622.*

ChunSoo et al., "In vitro cytotoxic activity of urushiol in the sap of Rhus verniciflua Stokes", Abstract to Journal of Korean Forestry Society, vol. 87, No. 2, pp. 260–269, (1998).*

Hwang et al., "A Study on the Cytotoxic Activity of Extract of Urushiol of Lacquer Sap Against L–5178Y Cells", Abstract to Korean J Biochem, 10(1), pp. 17–22, 1979.*

* cited by examiner

*Primary Examiner*—Dwayne C. Jones
(74) *Attorney, Agent, or Firm*—Cantor Colburn LLP

(57) ABSTRACT

Transitional cell carcinoma of the bladder is effectively treated by intravesical installation of urushiol. The urushiol appears to function as an intracellular hapten to help create an immunological reaction in localized tissues.

5 Claims, No Drawings

URUSHIOL THERAPY OF TRANSITIONAL CELL CARCINOMA OF THE BLADDER

This application claims benefit of Provisional Application Ser. No. 60/108,115 filed Nov. 12, 1998.

BACKGROUND OF THE INVENTION

1. Field of the Invention

The invention relates to the field of treating carcinomas. More particularly, the invention relates to the regression and prevention of recurrence of transitional cell carcinoma in the bladder.

2. Prior Art

Conventionally, intravesical instillation of Bacille Calmette-Guerin (BCG) has been favored as the most effective therapy for superficial transitional cell carcinoma of the bladder. Such treatment with BCG is believed to create a local immunological reaction evidenced by cytokines and cytotoxic T cells in the urine of the patient following therapy. The cytokines indicate a coordinated antibody and T cell immune interaction and the cytotoxic T cells appear to lyse the carcinoma cells. While treatment of the patient with BCG is considered an effective treatment, drawbacks of BCG include liver and pulmonary dysfunction and disease. Because of the drawbacks many patients cannot tolerate such treatment. In addition, up to thirty percent of patients do not respond to the treatment.

Other contemporary treatments include keyhole limpet hemocyanin and mistletoe extract as a lectin. While both of these treatments show promise, they are experimental and unproven. Other immunotheraputic agents that have been investigated include interferons, and interleukin-2.

Thus, the medical art concerned with the treatment of transitional cell carcinoma of the bladder is in need of alternate treatment methods without the side effects noted above.

SUMMARY OF THE INVENTION

The above-identified drawbacks of the prior art are overcome or alleviated by the urushiol therapy of the invention.

Urushiol, the active immunogen in toxicodendron radicans (poison ivy) is employable through intravesical instillation to treat transitional cell carcinoma of the bladder. A water soluble analogue of urushiol is preferably instilled in the bladder and retained therein for a selected period of time and then drained through the same catheter by which it was instilled. The necessity and frequency of repeated treatments are then determined based upon local inflammatory response and the rate of success of the treatment. These are monitored preferably by interval cystoscopy. The urushiol composition instilled in the bladder creates significant local immune response in patients including those with immunosuppressed conditions.

The urushiol composition is preferably instilled in the bladder by a foley catheter with the composition being either a suspension or colloid or a solution.

DETAILED DESCRIPTION OF THE PREFERRED EMBODIMENTS

Carcinoma of the bladder is a common clinical problem in the United States (in excess of fifty thousand new cases and twelve thousand deaths per year) and around the world. Treatments, therefore, are important to a large number of people. Treatments exist as stated above but with many people being precluded from such treatment for a variety of reasons, further research in the area is ongoing. Due to the high demand for effective treatments, the new treatment as described herein was developed.

As noted, urushiol is a component of common poison ivy. In its natural form, urushiol is lipid soluble, which may make the compound difficult to administer. Thus, analogues having aqueous solubility are preferred for the invention. It should be noted, however, that the lipid soluble form may also be employed. Initial methodology is to administer one part per million concentration which is then increased or decreased depending upon clinical response.

Urushiol in an aqueous or liquid soluble form or in suspension or colloid or a solution, introduced to the bladder of a patient by catheter, preferably foley catheter, results in a marked local immune response, the severity of which is controllable by timing installations and controlling the concentration of the composition instilled.

The immune response to urushiol is retained even in immunosuppressed patients for reasons that are not currently known but are thought to be due to the identity of the effector T cells. Since immunosuppression is common in many combined treatments of cancer, the property is of particular importance.

Alternate methods of applying urushiol to the transitional cell lining of the bladder might include distending the bladder by gas(rather than by saline) cystoscopy and then painting specific areas within the bladder with the urushiol composition. An aerosol spray containing urushiol or an analogue could also be employed through a nozzle whose direction could be controlled. This aerosol or painting approach could also be applied to the therapy of the surface of other types of tumors.

Urushiol spurs an increase in cytokine level and cytotoxic T cells in the local area within the bladder. It is believed that the immunological reaction is due to the urushiol functioning as an intracellular hapten, thus conjugating extracelluar proteins and penetrating cell membranes to conjugate intracellular proteins thereby enabling it to organize a multifront immune attack on the specified transitional cell carcinoma. The planned iatrogenic allergic cystitis caused by the local application of urushiol will be a form of Delayed Hypersensitivity Reaction.

Urushiol is known to exist in many forms and it is to be understood that the forms contemplated in the invention include but are not limited to: urushiol, water soluble derivatives of urushiol, tetrahydrourushiol glycoside, 3-alky catechols, 3-alkylene catechols having from one to five sites of unsaturation, 3-pentadecylcatechol and 3-pentadecylcatechol having from one to five sites of unsaturation.

An effective amount of urushiol is instilled followed by repeat instillations on a weekly to monthly basis depending upon internal observation via cystoscopy and particular patient reaction. It is unlikely that the substance could be retained in the bladder for longer than two or three hours due to the natural bladder filling by urine excretion. The bladder is then drained and the catheter removed. An alternative method of application is, as stated above, painting or spraying the tissue targeted. In essence, the alternative treatment is direct as opposed to a more general treatment of the organ affected. An advantage of the specific target treatment method is that general bladder irritation might be less severe or avoided altogether.

It should be further understood that the urushiol immunotherapy that is described hereinabove is also effective for other malignant tumors as an active nonspecific type treatment. A local injection into or onto the tumor itself can create an immune reaction having beneficial effects such as eradication of the tumor or retardation of the growth thereof. Another alternate method for treating tumors is to process urushiol in a cell culture and then reintroduce the processed cells into systemic circulation. The processed cells would then be programmed to incite the immune response.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A topically applicable carcinoma treatment composition in suspension, colloid, or solution form comprising urushiol, water soluble derivatives of urushiol, tetrahydrourushiol glycoside, 3-alky catechols, 3-alkylene catechols having from one to five sites of unsaturation, 3-pentadecylcatechol, and 3-pentadecylcatechol having from one to five sites of unsaturation.

2. A method for treating transitional cell carcinoma of the bladder comprising:

catheterizing a patient;

instilling through said catheter a composition comprising an effective amount of urushiol;

retaining said composition in the bladder for a selected period of time; and draining said composition.

3. A method for treating transitional cell carcinoma of the bladder as claimed in claim 2 wherein said catheterizing is by a foley catheter.

4. A method for treating transitional cell carcinoma of the bladder as claimed in claim 2 wherein said urushiol is in one of a suspension, colloid or solution and is in the range of about 0.0000001% to about 100%, urushiol, water soluble derivatives of urushiol, tetrahydrourushiol glycoside, 3-alky catechols, 3-alkylene catechols having from one to five sites of unsaturation, 3-pentadecylcatechol and 3-pentadecylcatechol having from one to five sites of unsaturation.

5. A method for treating transitional cell carcinoma of the bladder as claimed in claim 2 wherein said method further includes internal examination by cystoscopy.

* * * * *